US00PP22206P2

(12) United States Plant Patent
Austin

(10) Patent No.: US PP22,206 P2
(45) Date of Patent: Oct. 25, 2011

(54) ***ROSA HYBRIDA* SHRUB NAMED 'AUSCHARIOT'**

(50) Latin Name: *Rosa hybrida shrub.*
Varietal Denomination: AUSchariot

(75) Inventor: David C. H. Austin, Wolverhampton (GB)

(73) Assignee: David Austin Roses Ltd., Albrighton, Wolverhampton (GB)

( * ) Notice: Subject to any disclaimer, the term of this patent is extended or adjusted under 35 U.S.C. 154(b) by 0 days.

(21) Appl. No.: 12/802,885

(22) Filed: Jun. 15, 2010

(51) Int. Cl.
*A01H 5/00* (2006.01)

(52) U.S. Cl. ..... Plt./108

(58) Field of Classification Search ..... Plt./108
See application file for complete search history.

*Primary Examiner* — Susan McCormick Ewoldt
(74) *Attorney, Agent, or Firm* — Kauth, Pomeroy, Peck & Bailey LLP

(57) ABSTRACT

A variety of rose plant of the shrub class, named 'AUSchariot'. The 'AUSchariot' rose is a plant suitable for repeat cut flower production having bright crimson buds that gradually open to reveal many-petalled, deep red blooms with a light, fruity fragrance and long vase life, produced on strong upright stems.

1 Drawing Sheet

Classification: The present invention relates to a new *Rosa hybrida* shrub.

Variety denomination: The new plant has the varietal denomination 'AUSchariot'.

CROSS-REFERENCE TO RELATED APPLICATIONS

The current application claims priority to a European Breeder's Right Certificate Application No. CPVO 2010/1102, filed May 25, 2010, the disclosure of which is incorporated herein by reference.

ORIGIN OF INVENTION

This invention relates to a new and distinct variety of shrub rose plant named 'AUSchariot', which was originated by cross pollination of two unnamed, unpatented varieties of *Rosa hybrida*.

BACKGROUND OF THE INVENTION

The primary objective of this breeding was to produce bright crimson buds that gradually open to reveal many-petalled, deep red blooms with a light, fruity fragrance and long vase life, produced on strong upright stems which are suitable for year round cut flower production under standard greenhouse conditions.

SUMMARY OF THE INVENTION

Among the features which distinguish the new variety from other presently available and commercial rose cultivars known to the inventor is the following combination of characteristics: double, deep red blooms, stamens that are revealed as the flower ages, a light, fruity fragrance, strong upright stems suitable for cut flower use, and a long vase life.

Asexual reproduction of the new variety by cutting as performed in greenhouses at Bowling Green Lane in Albrighton, Britain shows that the foregoing and other distinguishing characteristics come true to form and are established and transmitted through succeeding asexual propagations. 'AUSchariot' may be asexually propagated by cutting.

COMPARISON WITH PARENTS

The new rose may be distinguished from its seed parent, by the following combination of characteristics: whereas the seed parent has blooms that are a lighter shade of red and are rosette shaped, 'AUSchariot' bears double blooms of a deep red.

The new variety may be distinguished from its pollen parent, by the following combination of characteristics: whereas the pollen parent has orange-colored blooms with no form and poor lastingness, 'AUSchariot' has deep red blooms that have a long vase life.

COMPARISON WITH THE CLOSEST COMMERCIALLY AVAILABLE CULTIVAR

The closest commercially available cultivar to the new variety is the 'AUSdecorum' (U.S. Plant Pat. No. 18717). The new rose may be distinguished from the 'AUSdecorum' variety by the following combination of characteristics: the 'AUSdecorum' has far fewer petals than does the 'AUSchariot', and the 'AUSdecorum' has much stronger sepal extensions. In addition, the leaves of the 'AUSchariot' are matte, compared to the semi-glossy foliage of 'AUSdecorum'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

The following description is of 2 year-old rose plants of the new variety grown indoors in a greenhouse in Albrighton, Britain in the month of July. Phenotypic expression may vary with environmental, cultural and climatic conditions, as well as differences in conditions of light and soil.

FLOWER CHARACTERISTICS

Blooming habit: Continuous. The number of blooms per plant during the growing season is profuse, but there are too many to count.

Bud:

*Size.*—About 2 cm long and 1.7 cm in diameter when the petals start to unfurl.

*Form.*—The bud form is short.

*Color.*—When sepals first divide, the bud color is red-purple RHS 61A. When half blown, the upper sides of the petals are red-purple RHS 61A, and the lower sides of the petals are red-purple RHS 60B.

*Calyx.*—Shape: (from above) star-shaped, with the sepals folding right back when the flower is fully open. Length: 5 cm. Diameter: 1 cm.

*Sepals.*—Arrangement: regular. Color: Upper Surface: grayed-green RHS 191B. Lower Surface: yellow-green RHS 144B. Length: 2.9 cm. Width: 1 cm. Shape: triangular. Margin: slightly hairy. Surface texture: Upper Surface: downy. Lower Surface: smooth. Number: There are three normally appendaged sepals. There are 2 unappendaged sepals with slightly hairy edges.

*Receptacles.*—Color: yellow-green RHS 144A. Shape: funnel. Size: medium, about 0.8 cm×1 cm. Surface: smooth.

*Peduncle.*—Length: medium, averaging about 5 cm. Surface: smooth. Color: yellow-green RHS 144A. Strength: strong.

Blooms:

*Size.*—Large, average open diameter is about 10 cm.

*Borne.*—Singly.

*Stems.*—Strength: strong, average length is about 65 cm. Diameter: 6 mm.

*Form.*—When first open, bloom is cupped.

*Permanence of bloom.*—Outer petals curl back.

Petalage: Number of petals under normal conditions: 125.

*Color.*—The upper sides of the petals are red-purple RHS Group 61B. The reverse sides of the petals are red-purple RHS 61B. The base of the petals has a yellow spot of RHS 2C.

*Discoloration.*—General tonality at end of first day is red-purple RHS 61 B, and at the end of the third day is purple RHS 61A.

*Fragrance.*—Slight. Character of fragrance: fruity.

Petals:

*Texture.*—Velvety.

*Size.*—Width: 4 mm. Length: 4 mm.

*Surface.*—Smooth.

*Shape.*—Obovate.

*Margin.*—Mostly entire, with some notched.

*Apex shape.*—Mostly rounded.

*Base shape.*—Obovate.

*Form.*—Slightly incurved.

*Arrangement.*—Imbricated.

*Petaloids.*—Number: 12. Color: red-purple RHS 61 B. Length: 10 mm. Width: 8 mm. Shape: Obovate. Margin: Irregular.

*Persistence.*—Petals drop off cleanly before drying.

*Lastingness.*—On the plant: not tested. As a cut flower: long, about 11 days.

Reproductive parts:

*Stamens.*—Number: 50. Length: 7 mm.

*Anthers.*—Length: 2 mm. Color: grayed-yellow RHS 162A. Arrangement: Regular around styles, and mixed with a few petaloids.

*Filaments.*—Color: yellow RHS 10C. Length: 5 mm.

*Pollen.*—Color: grayed-yellow RHS 162A.

*Pistils.*—Number: 80. Length: 8 mm.

*Styles.*—Color: grayed-yellow RHS 160B. Length: 7 mm.

*Stigmas.*—Color: grayed-yellow RHS 160B. Length: 1 mm.

*Hips.*—None Observed.

PLANT CHARACTERISTICS

Plant form: Shrub.

Plant growth: Medium.

Age to maturity: One year to 18 months.

Mature plant: Height: 0.9 m. Width: 0.9 m.

Foliage:

*Number.*—Leaflets on normal mid-stem leaves is: 7 (including terminal leaflet).

*Size.*—Large, about 16 cm long×9 cm wide. Quantity: Normal. Number of leaves per flowering stem is: 9.

*Color.*—New foliage: Upper side: (yellow-green) RHS 144A, overlaid with (grayed-purple) RHS 184A. Lower side: (grayed-purple) RHS 184B. Old foliage: Upper side: (dark green) RHS 139A. Lower side: grayed-green RHS 191A.

Leaflets:

*Size.*—About 7 cm long×4 cm wide.

*Shape.*—Broadly Oval.

*Base shape.*—Rounded.

*Apex shape.*—Acuminate.

*Texture.*—Semi-glossy.

*Edge.*—Serrated.

*Serrations.*—Single.

*Petiole.*—Color: (green) RHS 138B. Length: 2.5 cm. Width: 0.25 cm. Surface Texture: prickly.

*Petiole rachis.*—Color: (grayed-red) RHS 182B. Underside: with prickles.

*Stipules.*—Length: 2 cm, smooth. Color: (green) RHS 138B.

*Auricle.*—Shape: sword-shaped. Length: 6 mm. Width: 1.5 mm. Color: (green) RHS 138B.

*Vein color.*—Green RHS 138A.

*Venation pattern.*—Reticulate.

Wood:

*New wood.*—Color: (green) RHS 139C. Bark: smooth.

*Old wood.*—Color: (green) RHS 139B. Bark: smooth.

Branching habit: Main stems are cut to allow a flowering step to shoot so no natural branching habit was observed.

Stems:

*Mature stem.*—Length: 70 cm. Diameter: 8 mm.

*Internode distance.*—60-100 mm. The above measurements are all variable, depending on growing conditions in a season.

*Stem Pubescence Present.*—No.

Prickles:

*Quantity.*—On main canes from base: ordinary, Number per stem length: 15 per 20 cm. On laterals from main canes: ordinary. Number per stem length: 10 per 20 cm.

*Form.*—Concave curved inward.

*Length.*—9 mm.

*Color when young.*—(Grayed-purple) RHS 184B.

*Color when mature.*—(Grayed-orange) RHS 166C.

Small prickles:

*Quantity.*—Main stalk: many. Number per stem length: 30 per 20 cm. Laterals: few. Number per stem length: 5 per 20 cm.

*Color.*—When young: (grayed-purple) RHS 1848. When mature: (grayed-orange) RHS 177C.

Disease resistance:

*Mildew.*—Resistant.

*Blackspot.*—Resistant.

*Rust.*—Resistant.

Pest resistance: Not tested.

Winter hardiness: Not tested.

Growing conditions: Special. Greenhouse rose for cut flower production; disbudded where necessary to leave on bloom per stem.

What is claimed is:

1. A new and distinct variety of rose plant of the shrub class suitable for repeat flower production, substantially as herein shown and described.

* * * * *

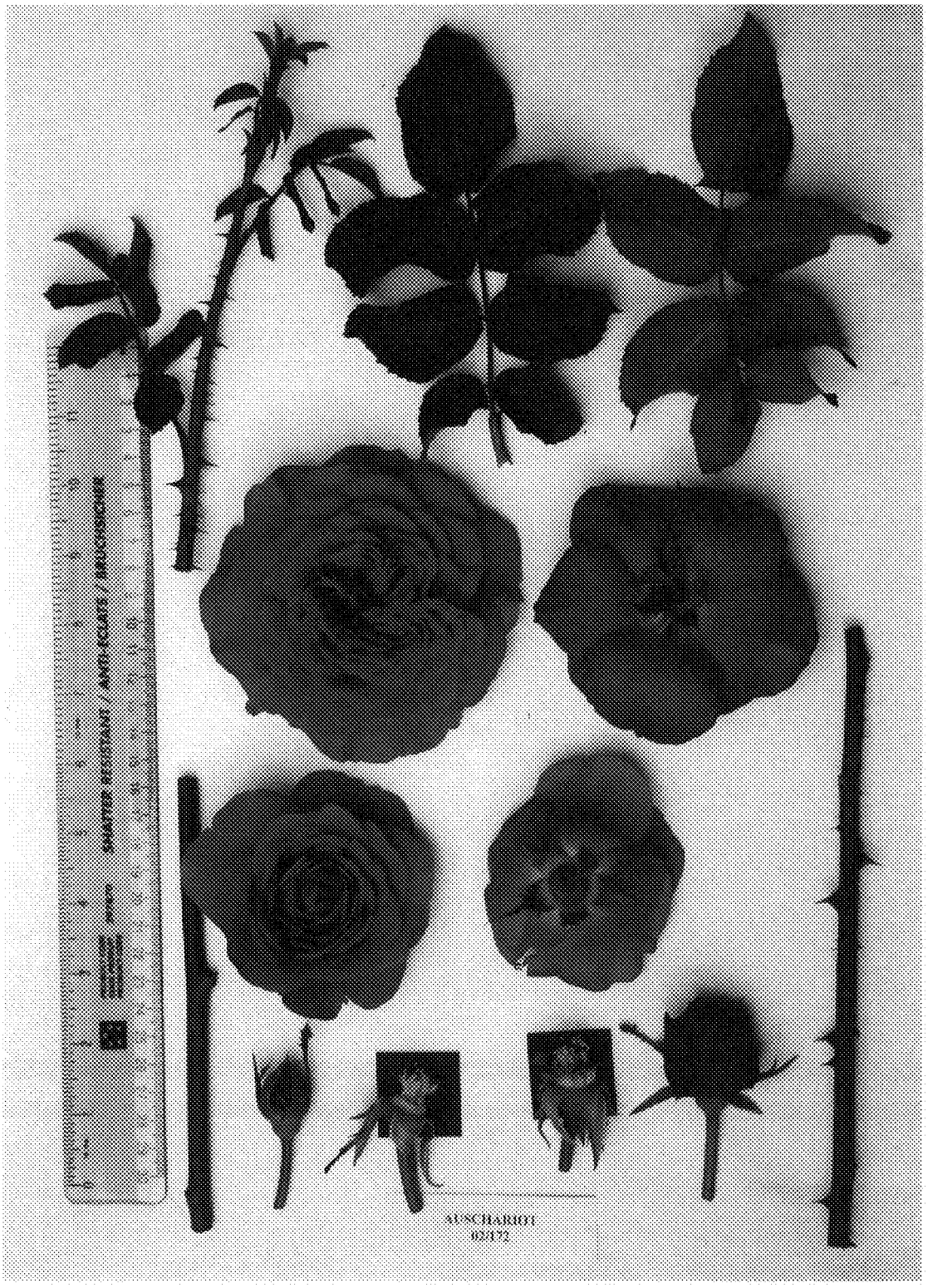
AUSCHARIOT
02A72

UNITED STATES PATENT AND TRADEMARK OFFICE

CERTIFICATE OF CORRECTION

PATENT NO. : PP22,206 P2
APPLICATION NO. : 12/802885
DATED : October 25, 2011
INVENTOR(S) : David C. H. Austin It is certified that error appears in the above-identified patent and that said Letters Patent is hereby corrected as shown below:

In column 5, line 14, delete “1848” and add --184B--

Signed and Sealed this
Seventh Day of February, 2012

David J. Kappos

David J. Kappos
*Director of the United States Patent and Trademark Office*